United States Patent [19]

Rebafka et al.

[11] 4,319,055

[45] Mar. 9, 1982

[54] PROCESS FOR REMOVING FORMALDEHYDE FROM AQUEOUS SOLUTIONS OF BUT-2-YNE-1,4-DIOL

[75] Inventors: Walter Rebafka, Eppelheim; Gerd Heilen, Speyer; Werner Fliege, Otterstadt, all of Fed. Rep. of Germany

[73] Assignee: BASF Aktiengesellschaft, Ludwigshafen, Fed. Rep. of Germany

[21] Appl. No.: 174,649

[22] Filed: Aug. 1, 1980

[30] Foreign Application Priority Data

Aug. 4, 1979 [DE] Fed. Rep. of Germany ....... 2931692

[51] Int. Cl.$^3$ .................... C07C 29/88; C07C 33/046
[52] U.S. Cl. ................................................ 568/856
[58] Field of Search ......................................... 568/856

[56] References Cited

U.S. PATENT DOCUMENTS

| | | | |
|---|---|---|---|
| 2,414,576 | 1/1947 | Wyler | 568/854 |
| 2,532,252 | 11/1950 | Wyler | 568/854 |
| 2,993,078 | 7/1961 | Hort | 568/856 |
| 3,129,252 | 4/1964 | Graham et al. | 568/856 |
| 3,130,236 | 4/1964 | Shull | 568/856 |
| 3,232,996 | 2/1966 | Graham et al. | 568/856 |
| 4,104,162 | 8/1978 | Junkermann et al. | 210/759 |
| 4,180,687 | 12/1979 | Burrus et al. | 568/856 |

FOREIGN PATENT DOCUMENTS 2511432 10/1975 Fed. Rep. of Germany .

*Primary Examiner*—Joseph E. Evans
*Attorney, Agent, or Firm*—John H. Shurtleff

[57] ABSTRACT

A process for removing formaldehyde from aqueous solutions of but-2-yne-1,4-diol by treating the solutions with an alkaline agent at an elevated temperature in the presence of hydrogen peroxide.

7 Claims, No Drawings

PROCESS FOR REMOVING FORMALDEHYDE FROM AQUEOUS SOLUTIONS OF BUT-2-YNE-1,4-DIOL

The present invention relates to a novel process for removing formaldehyde from aqueous solutions of but-2-yne-1,4-diol.

It is known that the synthesis of but-2-yne-1,4-diol from acetylene and formaldehyde gives a product which contains from about 0.2 to 2% by weight of unconverted formaldehyde. Since this formaldehyde content interferes with the hydrogenation of butynediol to butane-1,4-diol, it has already been proposed to remove the formaldehyde from crude but-2-yne-1,4-diol before hydrogenation.

According to U.S. Pat. No. 3,232,996, this purification is effected by treating an aqueous solution of the formaldehyde-containing but-2-yne-1,4-diol with an alkaline agent, eg. sodium hydroxide, at from about 80° to 110° C. This process has the disadvantage that it requires a relatively long treatment time, namely about 3 hours. If the treatment is carried out at from 125° to 200° C. under pressure, as described in U.S. Pat. No. 3,130,236, a reaction time of from 2 to 8 hours is required. Furthermore, even after 8 hours' treatment, about 0.1% by weight of formaldehyde was still found to be present in the butynediol.

It is an object of the present invention to provide a process by means of which formaldehyde can be removed more completely and more rapidly from crude but-2-yne-1,4-diol.

We have found that this object is achieved and that formaldehyde is more advantageously removed from aqueous solutions of but-2-yne-1,4-diol if the treatment of the solutions with an alakline agent at an elevated temperature is carried out in the presence of hydrogen peroxide.

It is true that German Laid-Open Application DOS No. 2,511,432 discloses that formaldehyde-containing effluents can be detoxicated by treatment with hydrogen peroxide and an alkali. However, given the known sensitivity of but-2-yne-1,4-diol to hydrogen peroxide, it was not to be expected that such thorough removal of formaldehyde from crude butynediol as is achieved by the novel process would be feasible without a reduction in the yield of butynediol. It is also surprising that the removal of formaldehyde in accordance with the invention takes place so rapidly, since the process described in German Laid-Open Application DOS No. 2,511,432 (see page 12) requires a reaction time of at least 20 minutes in the case of formaldehyde contents of less than 1% by weight.

Using the novel process, but-2-yne-1,4-diol, which has been obtained in a conventional manner by reacting acetylene with formaldehyde and which contains from 0.2 to 2% by weight of formaldehyde is treated, in aqueous solution, with an alkaline agent and hydrogen peroxide at an elevated temperature. The aqueous starting solutions contain from about 30 to 60% by weight of but-2-yne-1,4-diol.

Suitable alkaline agents are alkali metal hydroxides and alkaline earth metal hydroxides, sodium hydroxide and potassium hydroxide being preferred. Advantageously, the amount of alkaline agent used is from 80 to 120 mole %, preferably from 90 to 110 mole %, based on formaldehyde. The process is carried out at an elevated temperature, for example at from 50° to 150° C., preferably from 80° to 105° C., under atmospheric pressure. The hydrogen peroxide is used in an amount of from 80 to 120, preferably from 90 to 110, mole % (theoretical requirement: 100%), based on formaldehyde.

The residence time used is less than 60 minutes and preferably less than 10 minutes. This, surprisingly, removes formaldehyde to the extent of leaving a residual amount of less than 100 ppm.

EXAMPLE 1

A tubular reactor of 4 mm diameter and 20 ml capacity is heated to 80° C. in an oil bath. Per hour, 250 ml of a mixture of 1,000 parts by weight of butynediol, in the form of a 40% strength aqueous solution containing 0.5% by weight of formaldehyde, based on the aqueous solution, 9.5 parts by weight of a 30% strength aqueous hydrogen peroxide solution and 13.3 parts by weight of a 50% strength aqueous sodium hydroxide solution are passed through the tubular reactor. The mixture leaving the reactor is collected in a stirred flask and is continuously brought to a pH of from 3 to 4 by adding formic acid. Analysis of the aqueous mixture indicates a formaldehyde content of less than 100 ppm. The butynediol employed is found to be unchanged. The mixture obtained can be employed directly for a subsequent synthesis of butanediol by hydrogenation.

EXAMPLE 2

The procedure described in Example 1 is followed, but the tubular reactor is heated to 100° C. and 400 ml per hour of the starting mixture are passed through it. Analysis of the butynediol solution thus obtained shows a formaldehyde content of 0.007% by weight.

EXAMPLE 3

The procedure described in Example 1 is followed, but the tubular reactor is heated to 100° C. and 350 ml per hour of a mixture of 1,000 parts by weight of butynediol, in the form of a 40% strength aqueous solution containing 0.86% by weight of formaldehyde, based on aqueous solution, 16.2 parts by weight of a 30% strength aqueous hydrogen peroxide solution and 22.9 parts by weight of a 50% strength aqueous sodium hydroxide solution are passed through the tube. Analysis of the butynediol solution thus obtained shows a formaldehyde content of 0.006% by weight.

We claim:

1. In a process for removing formaldehyde from an aqueous solution of but-2-yne-1,4-diol by treating the solution with an alkaline agent at an elevated temperature, the improvement which comprises carrying out the treatment with said alkaline agent in the presence of hydrogen peroxide at a temperature from 50° to 150° C., the hydrogen peroxide being used in an amount of 80 to 120 mole % based on the formaldehyde to be removed.

2. A process as claimed in claim 1 wherein the residence time of the but-2-yne-1,4-diol being treated is less than 10 minutes but sufficient to remove formaldehyde down to a residual content of less than 100 ppm.

3. A process as claimed in claim 2 wherein the treatment temperature is 80° to 105° C.

4. A process as claimed in claim 1 wherein the initial aqueous solution being treated contains about 30 to 60% by weight of but-2-yne-1,4-diol and 0.2 to 2% by weight of formaldehyde, and the amount of alkaline agent used is from 80 to 120 mole % based on the formaldehyde.

5. A process as claimed in claim 4 wherein the alkaline agent is selected from the group consisting of sodium hydroxide and potassium hydroxide.

6. A process as claimed in claim 4 wherein said amount of hydrogen peroxide is 90 to 110 mole %.

7. A process as claimed in claim 4 wherein the treatment is carried out at a temperature of 80° to 105° C. and for a period of time, sufficient to remove formaldehyde down to a residual content of less than 100 ppm.

* * * * *